(12) United States Patent
Ebara

(10) Patent No.: US 11,344,333 B2
(45) Date of Patent: May 31, 2022

(54) BONE FIXATION DEVICE

(71) Applicant: MIZUHO CORPORATION, Tokyo (JP)

(72) Inventor: Sohei Ebara, Kanagawa (JP)

(73) Assignee: MIZUHO CORPORATION, Tokyo (JP)

( * ) Notice: Subject to any disclaimer, the term of this patent is extended or adjusted under 35 U.S.C. 154(b) by 0 days.

(21) Appl. No.: 16/637,350

(22) PCT Filed: Aug. 10, 2017

(86) PCT No.: PCT/JP2017/029143
§ 371 (c)(1),
(2) Date: Feb. 7, 2020

(87) PCT Pub. No.: WO2019/030902
PCT Pub. Date: Feb. 14, 2019

(65) Prior Publication Data
US 2021/0161563 A1    Jun. 3, 2021

(51) Int. Cl.
*A61B 17/70*    (2006.01)
(52) U.S. Cl.
CPC ............................... *A61B 17/7032* (2013.01)
(58) Field of Classification Search
CPC ............ A61B 17/7035; A61B 17/7049; A61B 17/7044; A61B 17/7067; A61B 17/701; A61B 17/7055; A61B 17/7062; A61B 17/7034; A61B 17/7056; A61B 17/7032–17/704
See application file for complete search history.

(56) References Cited

U.S. PATENT DOCUMENTS

| | | | |
|---|---|---|---|
| 10,499,954 B2 * | 12/2019 | Unger | A61B 17/7047 |
| 2003/0130659 A1 | 7/2003 | Haider | |
| 2007/0016189 A1 | 1/2007 | Lake et al. | |
| 2007/0161990 A1 | 7/2007 | Hillyard et al. | |
| 2008/0114401 A1 | 5/2008 | Liu et al. | |
| 2016/0058478 A1 * | 3/2016 | Agarwal | A61B 17/7035 606/270 |

FOREIGN PATENT DOCUMENTS

| | | |
|---|---|---|
| EP | 2684533 A1 | 1/2014 |
| JP | 2002-528218 A | 9/2002 |
| JP | 2008-544815 A | 12/2008 |
| WO | 2009/133539 A1 | 11/2009 |
| WO | WO-2009133539 A1 * | 11/2009 ......... A61B 17/7047 |

OTHER PUBLICATIONS

Official Action from corresponding European Application No. 17921012.5 dated Mar. 17, 2021.

* cited by examiner

*Primary Examiner* — Pedro Philogene
(74) *Attorney, Agent, or Firm* — Porter Wright Morris & Arthur LLP

(57) ABSTRACT

To provide a bone fixation device able to firmly fix bone elements.
A bone fixation device, comprising: a base section having a first space that holds a rod; a hook formed with a second space in which a bone element is accommodated together with a art of the base section; and a sandwiching part that is installed to the base section and that sandwiches the bone element which has been accommodated in the second space together with a pail of the hook, wherein the sandwiching part is shiftable allowing attachment to the bone element.

7 Claims, 5 Drawing Sheets

BONE FIXATION DEVICE

TECHNICAL FIELD

The present invention relates to a bone fixation device that connects with a rod and is then fixed to bones.

BACKGROUND ART

For example, in general spinal fixation methods implemented for the correction and stability of spinal curvature, a spine is fixed with a pair of flexible rods arranged parallel with the spine. Those rods are equipped with some fixation means such as hooks or screws to be fixed to various vertebrae along the spine.

Thus, the rod is used in combination with the fixation means such as the hooks or screws and can fix vertebrae or other bone elements to each other.

Now, a bone hook as a fixation means is provided with a main body into which a rod is installed and a hook with a curved arm. The rod is fixed to the main body, and the bone elements of vertebrae are hooked to the arm so that the arm can be fixed (see Patent Literature 1).

PRIOR ART DOCUMENTS

Patent Literature

Patent Literature 1: JP 2002-528218 (A)

SUMMARY OF INVENTION

Problems to be Solved by Invention

The general bone hook as described above is normally hooked to bone elements for fixation, so that the bone hook is easily detached therefrom. Further, the bone hook is not screwed into bones like bone screws, so that it cannot firmly fix the bone elements like bone screws.

Thus, the present invention has been made for solving the above problems and provides a bone fixation device able to firmly fix bone elements.

Means to Solve Problems

For solving the above problems, the following structures are adopted in this invention. Note that referential numerals for figures are given in parentheses to make it easy to understand the present invention, but the present invention should not be limited to those numerals.

That is, a bone fixation device (S) recited in aspect 1 comprises: a base section (20) having a first space (21) that holds a rod (7); a hook (30) formed with a second space (31) in which a bone element (5) is accommodated together with a part of the base section; and a sandwiching part (40) that is installed to the base section and that sandwiches the bone element which has been accommodated in the second space together with a part of the hook, wherein the sandwiching part is shiftable, allowing attachment to the bone element.

Further, the bone fixation device recited in aspect 2 has a through hole (51) connecting between the first space and the second space, and the sandwiching part has a shaft section (61) formed with a screw, the screw being formed on the outer peripheral surface of the shaft section in which to be screwed together with a screw formed on the through hole, and the shaft section is shiftably arranged in the through hole in a vertical direction.

Still further, regarding the bone fixation device recited in aspect 3, in the bone fixation device according to aspect 1 or aspect 2 the bone element is held between a pair of surfaces comprising the sandwiching part and a part of the hook.

Yet still further, regarding the bone fixation device recited in aspect 4, in the bone fixation device according to any one of aspects 1 to 3, the base section has an opening (11) connecting with the first space, the opening allowing accommodation of the rod from the outside, and the opening is detachably provided with a covering body (15) that covers the opening.

Moreover, in the bone fixation device recited in aspect 5, in the bone fixation device according to any one of aspects 1 to 4, the sandwiching part is inclinable according to each shape of the bone element.

Effect of Invention

Bone elements are inserted into a space formed in a hook, and then a sandwiching part is adapted to contact the bone elements. Since the sandwiching part can hold the bone elements together with the hook within the space, the reliable fixation of the bone elements can be achieved.

Figure 3:
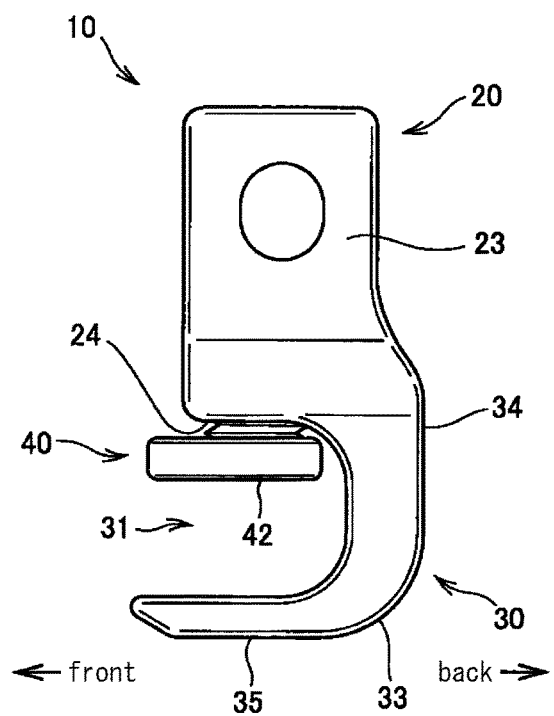
FIG. 3 This is the lateral diagram of the bone fixation device in the first embodiment.

Hereinafter, each embodiment of the present invention will be explained with reference to drawings, Note that the following explanation for a bone fixation device is one example, and the bone fixation device is herein explained as a bone hook S used in spinal fixation methods to be implemented for the correction and stability of spinal curvature. Further, for the sake of convenience, a crosswise direction in FIG. 3 is explained as a front-back direction of the bone hook S.

The First Embodiment

Figure 1:
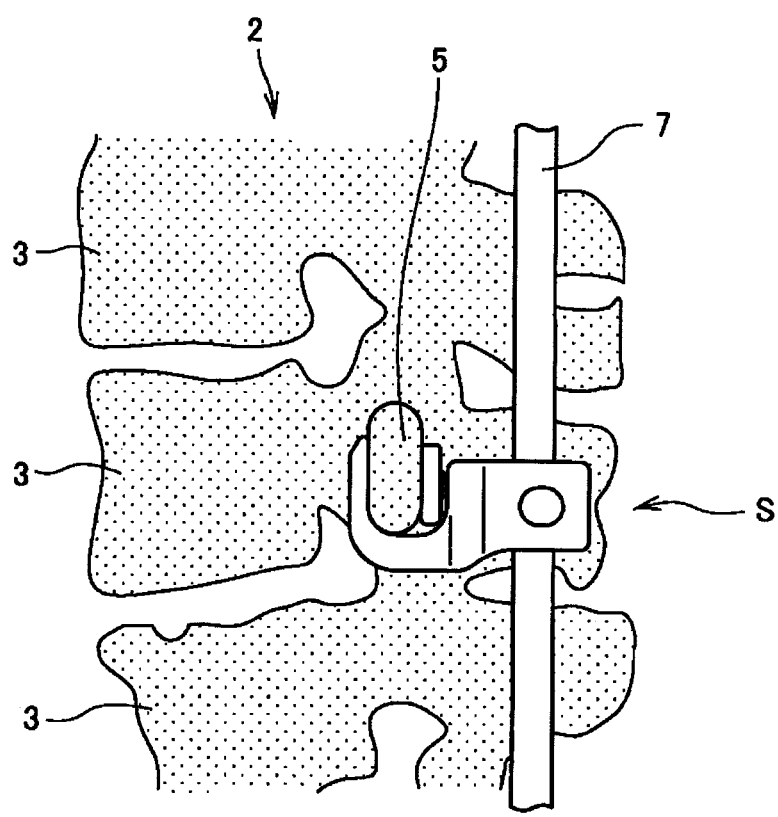
FIG. 1 This is the schematic diagram showing a condition that a bone fixation device in the first embodiment is installed to the bone elements of a spine.

As shown in FIG. 1, the bone hook S of the present embodiment is connected to a long-narrow cylindrical rod 7 arranged along a spine 2 and sandwiches a bone element 5, that is, protrusions and the like provided at a vertebra 3. Thus, the bone hook S fixes the spine 2 together with a plurality of screws or other bone hooks S (not shown) that are connected to the rod 7. Each screw is screwed into each vertebra 3 for fixation. By fixing the bone element 5 with the bone hook 5, the spine 2 or other bone elements 5 are fixed to each other.

Figure 2:
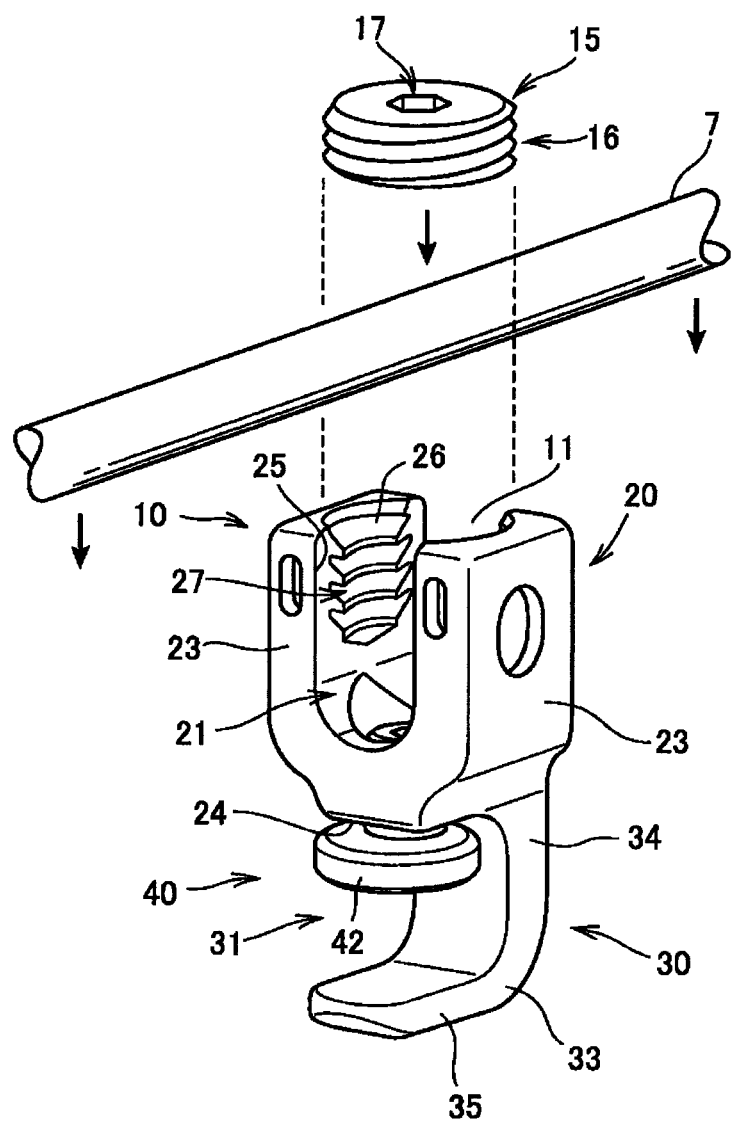
FIG. 2 This is the schematic diagram exemplifying the structure of the bone fixation device in the first embodiment.

As shown in FIG. 2, this bone hook S is provided with a main body 10 having an opening 11 at the top end thereof and a set screw 15 (a covering body in the present application) covering this opening 11. This bone hook S is formed of titanium or other proper metallic materials compatible with human bodies.

The main body 10 is provided with a base section 20 having a space 21 (the first space in the present application) in which the rod 7 can be accommodated and a hook 30 extending downward from the base section 20. The base section 20 and the hook 30 are integrally formed.

The base section 20 is provided with a lateral wall 23 surrounding each side portion of the base section 20 so as to form the space 21 and a bottom body 24 covering the bottom end of this lateral wall 23. At the lateral walls 23, 23 positioned in the front-back direction, an approximately U-shaped slot 25 connecting with the space 21 is formed. This slot 25 is connected with the opening 11 and allows the rod 7 to be inserted from the opening 11 along the slot 25. This rod 7 is then accommodated within the space 21.

Each upper inner-wall surface on the lateral wall 23 in the crosswise direction has an inner surface 26 circularly formed in a planar view, the inner surface 26 being formed with an inside screw 27.

As shown in FIG. 2, the set screw 15 is formed into approximately a cylindrical shape. The outer peripheral surface of the set screw 15 is formed with an outside screw 16 to be screwed together with the inside screw 27. The upper end surface of the set screw 15 has a concaved portion 17 as an engaging portion able to engage with polygonal tools. The set screw 15 can be rotated by using certain tools set at this concaved portion 17. The set screw 15 can be thus removed from the main body 10.

The set screw 15 is installed to the opening 11, so that the bottom end surface of the set screw 15 presses down the rod 7, the rod 7 being thus held within the space 21. Through this procedure, the main body 10 and the rod 7 are firmly fixed.

The hook 30 is used, for example, to fix the bone element 5 of the vertebra 3. This hook 30 has an arm 33 formed with a space 31 (the second space in the present application) in which the bone element 5 is accommodated. The space 31 has an opening in which the bone element 5 is laterally accommodated together with the base section 20.

The arm 33 has a curved section 34 extending downward from the base section 20 and a flat section 35 arranged approximately parallel with the bottom body 24 of the base section 20. The bone element 5 can be laterally accommodated in the space 31 formed by the bottom body 24 of the base section 20, the curved section 34 and the flat section 35.

Note that the flat section 35 or the bottom body 24 is not necessarily formed into a flat shape. It is also not necessary for the curved section 34 to be notably curved. As long as the bottom body 24 of the base section 20 and the arm 33 could form a space in which the bone element 5 can be accommodated, each shape thereof should not be limited.

In this manner, the bone element 5 of the vertebra 3 can be inserted into the space 31 from an opening laterally provided. The space 31 of the hook 30 thus allows the bone element 5 to be accommodated.

Further, the lower part of the base section 20 is provided with a sandwiching part 40 that holds the bone element 5 accommodated in the space 31 together with the flat section 35 of the hook 30.

The sandwiching part 40 is installed to the base section 20 in such a manner as to be vertically shiftable. The sandwiching part 40 allows contact with the bone element 5 to be inserted into the space 31 of the hook 30. This sandwiching part 40 has a primary section 42 that has a certain thickness and is formed into approximately a circular shape in a planar view, and a shaft 45 that is for shifting the primary section 42 vertically. The primary section 42 and the shaft 45 are connected to each other through a pin 46. The primary section 42 and the shaft 45 are held with a certain gap by the pin 46. With the imp, the primary section 42 is accommodable with some looseness.

Figure 4:
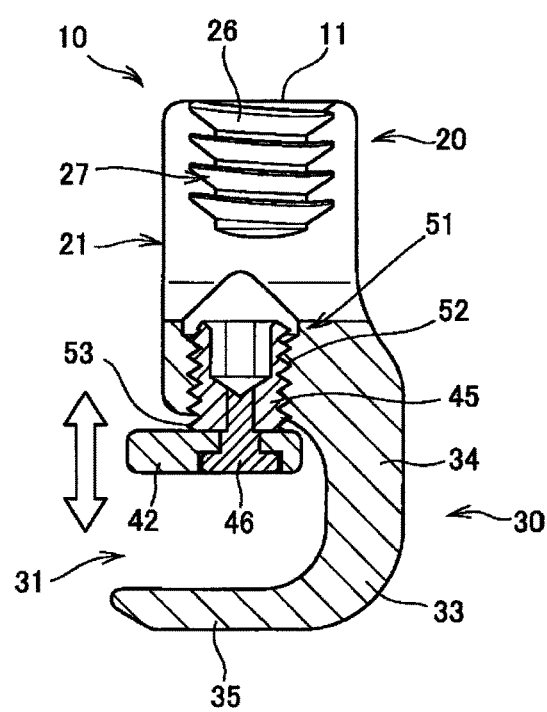
FIG. 4 This is the schematic diagram that shows the vertical section of the bone fixation device in the first embodiment and shows the installation condition of a sandwiching part.

As shown in FIG. 4, the front side of the bottom body of the base section 20 has a through hole 51 vertically extending, the shaft 45 being inserted into the thorough hole 51. The inner surface of this through hole 51 has an inside screw 52 while the outer circumference of the shaft 45 has an outside screw 53 able to be screwed together with this inside screw 52. As the arrow in FIG. 4 shows, for example, the shaft 45 is screwed into the through hole 51 by the clockwise rotation of the primary section 42. With this procedure, the primary section 42 moves away from the flat section 35 of the arm 33. On the other hand, through the counterclockwise rotation of the primary section 42, the shaft 45 is pulled outside from the through hole 51 so as to position the primary section 42 closer to the flat section 35 of the arm 33.

Accordingly, by rotating the primary section 42 in a certain direction, it is possible to adjust the distance between the primary section 42 and the flat section 35 of the hook 30. In the sandwiching part 40, according to each size of the bone element 5 to be inserted into the space 31 of the hook 30, the primary section 42 is shifted in a certain direction so as to allow the primary section 42 to be attached to the bone element 5. The bone element 5 is thus fixed by being held between the primary section 42 and the flat section 35.

As described above, in the bone hook S of the present embodiment, the bone element 5 that has been accommodated in the space 31 of the hook 30 is to be sandwiched between the flat section 35 of the hook 30 and the primary section 42. The bone element 5 is thus vertically pressed and fixed therebetween. Since the bone element 5 is sandwiched between the surface of the primary section 42 of the sandwiching part 40 and the surface of the flat section 35 of the hook 30, the bone element 5 can be firmly fixed.

Further, the shaft 45 and the primary section 42 of the sandwiching part 40 are connected with the pin 46. Thus, the shaft 45 and the primary section 42 are installed with certain looseness so that the surroundings of the sandwiching part 40 are vertically shiftable with this looseness. This allows the sandwiching part 40 to be inclined at a certain angle at the pin 46 as a fulcrum. Since this bone hook S of the present embodiment has the looseness, this enables that the surface of the sandwiching part 40 is easily attached to the bone element 5. Accordingly, this will disperse loads, so pressing-force evenly works relative to the bone element 5, allowing firmer fixation to the bone element 5.

In addition, although not shown in figures, the surface of the pin 46 having contact with the primary section 42 of the sandwiching part 40 may be convexly curved, so that the primary section 42 and the shaft 45 are connected to each other with a certain space therebetween. Comparing with the structure discussed above, this can incline the primary section 42 at more desirable angles. Thus, the primary section 42 can be inclined according to each external shape of the bone element 5 so it is possible to firmly sandwich the bone element 5 even if the surface of the bone element 5 are somewhat uneven.

In the present embodiment, the primary section 42 of the sandwiching part 40 and the shaft 45 are separately provided and connected to each other through pinned connection. However, those parts may be integrally formed. Further, connection methods between the primary section 42 and the shaft 45 are not limited to the pinned connection, but any methods would be applicable if they are generally known.

Furthermore, by expanding the length of the shaft 45 than the length of the through hole 51, the shaft 45 is easily exposed within the space 21 in which the rod 7 is housed. Through this application, while the rod 7 has been installed, the bottom end surface of the rod 7 presses down the shaft 45, which enables to easily prevent shifts of the primary section 42 due to the rotation of the shaft 45. Thus, comparing with the structure discussed above, this can further stably retain the fixation of the bone element 5.

Next, one example regarding operation effects of the bone hook S will be explained hereinbelow. In the present embodiment, the following methods will be explained: based on general spinal fixation methods implemented for the correction and stability of spinal curvature, certain bone elements 5 are fixed by the bone hook S.

First, an operator detaches the set screw 15 from the main body 10 with certain tools. The main body 10 is then installed at a certain position of the rod 7 arranged at the spine 2. Specifically, the rod 7 is inserted from the opening 11 of the base section 20, and after this rod 7 has been accommodated within the space 21, the set screw 15 is installed to the opening 11 with certain tools. In this condition, for easy installation of the bone element 5 into the space 31 formed in the hook 30, the set screw 15 is temporarily attached allowing that the main body 10 is rotatable at rod 7 as a fulcrum.

Second, according to the position of the bone element 5, the base section 20 that has been installed to the rod 7 is rotated so as to adjust the position of the hook 30. At the same time that the bone element 5 is accommodated in the space 31 of the hook 30, the primary section 42 of the sandwiching part 40 is rotated in a certain direction to shift downward according to the size of the bone element 5. The bone element 5 is thus sandwiched between the primary section 42 that has been attached to the bone element 5 and the flat section 35 of the hook 30.

Lastly, the set screw 15 is rotated in a certain direction so as to allow it to be screwed into the opening 11. The set screw 15 is then fixed, and this operation will be completed. Through this operation, the rod 7 is pressed downward by the set screw 15 and attached to the bottom body 24 of the base section 20 so as to fix the rod 7 relative to the main body 10. At the same time, the bone element 5 is held between the hook 30 and the sandwiching part 40 so as to be firmly fixed.

The Second Embodiment

Figure 5:
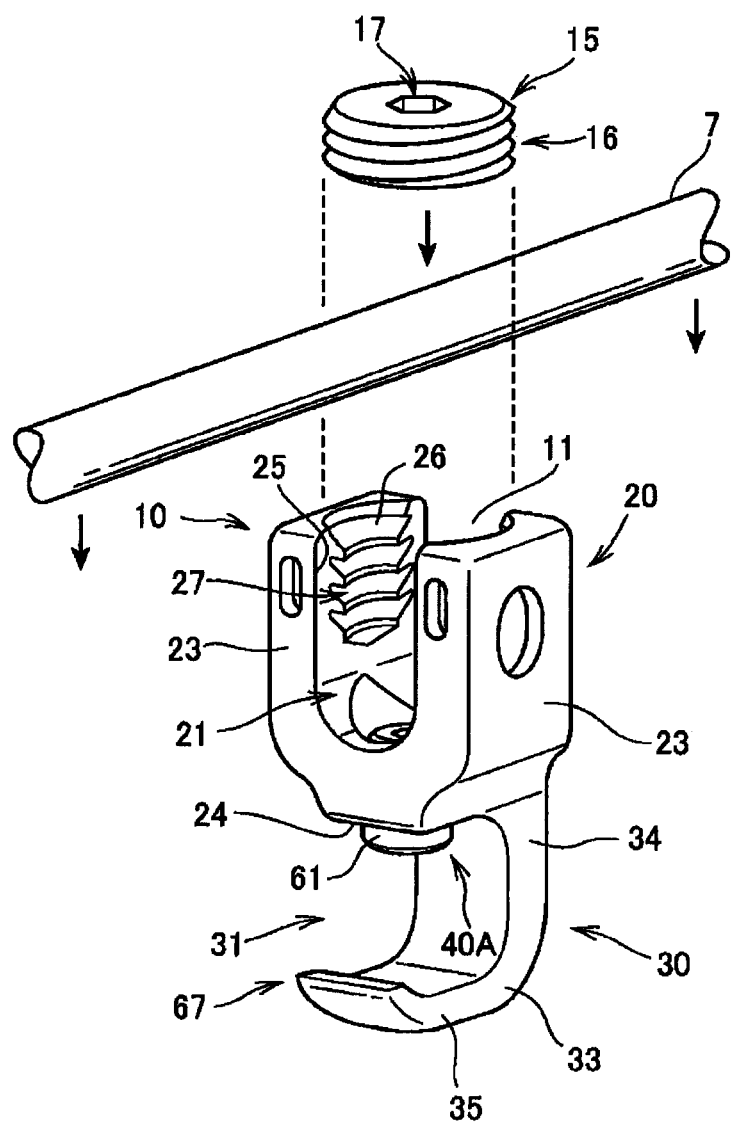
FIG. 5 This is the schematic diagram exemplifying the structure of the bone fixation device in the second embodiment.
Figure 6:
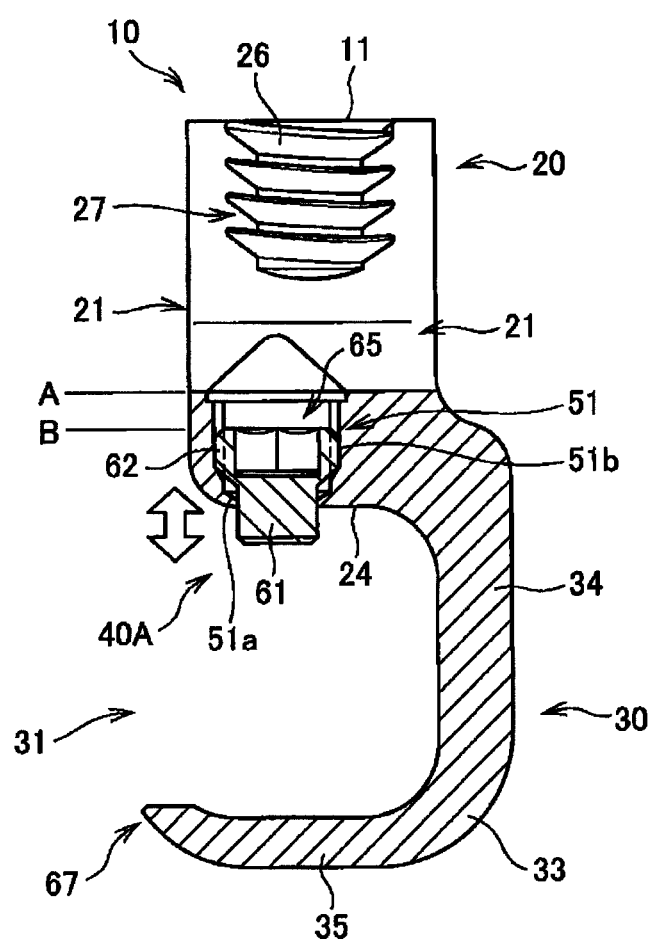
FIG. 6 This is the schematic diagram that shows the vertical section of the bone fixation device in the second embodiment and shows the installation condition of the sandwiching part.

Next, a bone hook S2 of the second embodiment will be explained with reference to FIGS. 5 and 6. In FIGS. 5 and 6, portions in common with FIGS. 2 and 4 will be assigned with the same referential numbers, and the detail explanation thereof will be omitted.

The second embodiment is different from the first embodiment in that the shape of the sandwiching part 40 is different. Specifically, as shown in FIG. 6, a sandwiching part 40A of the second embodiment is, for example, structured with a pin-shaped member having a head section 62 and a shaft section 61. The shaft section 61 may be set to a variety of lengths according to the size of the space 31 in the hook 30. The head section 62 is shiftable within the through hole 51 between a referential position A and a referential position B as indicated by FIG. 6. The tip end position of the shaft section 61 is arranged as follows: when the upper end of the head section 62 is placed at the referential position A, the tip end portion of the shaft section 61 forms approximately a smooth surface with the bottom surface of the bottom body 24 of the base section 20 and when the upper end of the head section 62 is placed at the referential position B, the length of the shaft section 61 is arranged so as to step into the space 31 of the hook 30 only for a certain length.

Although not shown in figures, the head section 62 is formed with outside screws on the outer peripheral surface thereof, so that the head section 62 is to be inserted into the through hole 51 connecting between the space 21 of the base section 20 and the space 31. The through hole 51 has a first hole part 51a with a diameter into which the shaft section 61 is insertable and a second hole part 51b with a diameter longer than the length of the first hole part 51a, the second hole part 51b accepting the insertion of the head section 62 thereinto. The second hole part 51b is formed with inside screws able to be screwed together with the outside screws formed on the outer peripheral surface of the head section 62.

Further, the upper end surface of the head section 62 is formed with a concavity 65 extending in a vertical direction. The shape of the concavity 65 corresponds to the tip shape of operational tools (not shown) to be connected with the sandwiching part 40A through outside operators. Thus, the concavity 65 can be fitted into those operational tools.

Each of the operational tools may be, for example, a stick-like member having a fitting part at the tip end thereof, the tip end accepting the fitting into the concavity 65 of the sandwiching part 40A. This fitting part is fitted into the concavity 65 of the sandwiching part 40A and by rotating the fitting part in a certain direction, as the arrow in FIG. 6 shows, the shaft section 61 of the sandwiching part 40A can shift in a vertical direction.

In the bone hook S2, by operating the sandwiching part 40A with operational tools, it is possible to adjust the distance between the tip end portion (bottom-end surface) of the shaft section 61 and the flat section 35 of the hook 30. In the sandwiching part 40A, according to the size of the bone element 5 to be inserted into the space 31 of the hook 30, the tip end portion of the shaft section 61 is shifted in a certain direction, allowing attachment to the bone element 5. By being sandwiched between the tip end portion of the shaft section 61 and the flat section 35, the bone element 5 is fixed.

A tip end portion 67 of the flat section 35 provided at the arm 33 is formed slightly protruded upward, so that this tip end portion 67 will enter a part of the bone element 5 when fixing the bone element 5. Thus, this makes the tip end portion 67 hard to pull out.

As discussed above, in the bone hook S of the present embodiment, the bone element 5 that has been accommodated in the space 31 of the hook 30 is sandwiched between the flat section 35 of the hook 30 and the shaft section 61 of the sandwiching part 40A. Thus, the bone element 5 is vertically pressed and fixed. In other words, the bone element 5 is held between the tip surface of the shaft section 61 of the sandwiching part 40A and the surface of the flat section 35 including the tip end portion of the hook 30. The bone element 5 is thus firmly fixed.

Note that the tip of the shaft section 61 of the sandwiching part 40A of the present embodiment is formed into a flat surface, however, it may be an inclined surface by projecting the front side of the shaft section 61 downward. With this structure, the tip of the shaft section 61 can easily bite into the bone element 5 and can make it hard to pull out.

Next, one example regarding operation effects of the bone hook S2 of the present embodiment will be explained hereinbelow. In the present embodiment, the following methods will be explained: based on general spinal fixation methods implemented for the correction and stability of spinal curvature, certain bone elements 5 are fixed by the bone hook S.

First, according to the position of the bone element 5, the main body 10 is arranged, and the base section 20 is rotated so as to adjust the position of the hook 30. At the same time the bone element 5 is accommodated in the space 31 of the hook 30, the tip of operational tools is fitted into the concavity 65 of the sandwiching part 40A. By rotating operational tools, the shaft section 61 of the sandwiching part 40 is shifted downward, allowing attachment to the bone element 5. Thus, the bone element 5 is sandwiched between the tip of the shaft section 61 and the flat section 35 of the hook 30.

Next, the rod 7 is inserted into the slot 25 through the opening 11 of the base section 20, and the set screw 15 is then installed to the opening 11 with certain tools.

Through the above procedures, the rod 7 is fixed to the main body 10 while the bone element 5 is sandwiched between the hook 30 and the sandwiching part 40, being thus firmly fixed.

Note that the present embodiment exemplifies only one embodiment and should not be limited by the embodiments described hereinabove. For example, it may be possible that the structures of the first embodiment and the second embodiment are properly combined to each other. Further, the present embodiment exemplifies that the opening 11 is formed at the top of the base section 20, allowing the rod 7 to be inserted from the opening 11; however, the opening 11 may be formed on the lateral wall 23. Still further, the shape of the hook 35 may be optionally altered. That is, as long as the hook 35 has an opening on the side thereof, and as long as the hook 35 has the certain opening 31 with area enough for the bone element 5 to be accommodated, the hook 35 may be formed into any shape. Yet still further, in the present embodiment the shape of the primary section 42 of the switching part 40 is formed into a circular shape in consideration of handleability. However, the primary section 42 may be any shape.

In the second embodiment, the sandwiching part 40A is structured to have the head section 62 and the shaft section 61; however, the through hole 51 may be formed into a straight shape, and the sandwiching part 40A may be the shaft section 61 formed into a cylindrical shape.

S Bone hook
5 Bone element
7 Rod
30 Hook
21, 31 Space
40, 40A Sandwiching part

The invention claimed is:

1. A bone fixation device, comprising:
 a base section having a first space provided with a first inside screw, wherein a covering body is adapted to be installed along the first inside screw to hold a rod in the first space, the base section having a second inside screw;
 a hook forming a second space adapted to accommodate a bone element, the hook extending downwardly from a back side of the base section; and
 a sandwiching part that is operable to shift along the second inside screw to sandwich, together with a part of the hook, a bone element in the second space,
 wherein a center axis of the second inside screw is arranged on a front side of the base section, the center axis of the second inside screw being arranged at a front side of the bone fixation device relative to a center axis of the first inside screw, and
 wherein a tip end portion of the hook is arranged at a front side of the center axis of the second inside screw and configured to protrude upward.

2. The bone fixation device according to claim 1, wherein the sandwiching part is inclinable according to a shape of a bone element in the second space.

3. The bone fixation device according to claim 1,
 wherein a primary section of the sandwiching part is non-concentrically arranged relative to a shaft of the second inside screw.

4. The bone fixation device according to claim 1, wherein the first inside screw and the second inside screw each extend vertically within the base section.

5. The bone fixation device according to claim 1, wherein the first inside screw is accessible to receive a covering body at the top of the base section and the second inside screw is accessible to receive the sandwiching part at the bottom of the base section.

6. The bone fixation device according to claim 1, further comprising a covering body adapted to be installed along the first inside screw, and a rod adapted for arrangement parallel with a patient spine when the rod is held in the first space by the covering body.

7. The bone fixation device according to claim 1, wherein the tip end portion of the hook has a width in a direction perpendicular to a direction in which a rod held in the first space extends, the tip end portion of the hook being configured to protrude upward across the whole width.

* * * * *